United States Patent
Herring

(10) Patent No.: US 12,276,583 B2
(45) Date of Patent: Apr. 15, 2025

(54) SYSTEM FOR DETECTING THE CONCENTRATION OF GASES IN SOIL

(71) Applicant: Jamison Wayne Herring, Kings, IL (US)

(72) Inventor: Jamison Wayne Herring, Kings, IL (US)

( * ) Notice: Subject to any disclaimer, the term of this patent is extended or adjusted under 35 U.S.C. 154(b) by 142 days.

(21) Appl. No.: 17/759,556

(22) PCT Filed: Jan. 29, 2021

(86) PCT No.: PCT/US2021/015785
§ 371 (c)(1),
(2) Date: Jul. 27, 2022

(87) PCT Pub. No.: WO2021/155204
PCT Pub. Date: Aug. 5, 2021

(65) Prior Publication Data
US 2023/0085819 A1   Mar. 23, 2023

Related U.S. Application Data

(60) Provisional application No. 62/968,366, filed on Jan. 31, 2020.

(51) Int. Cl.
*G01N 1/22* (2006.01)
*A01B 79/00* (2006.01)
(Continued)

(52) U.S. Cl.
CPC ......... *G01N 1/2294* (2013.01); *A01B 79/005* (2013.01); *G01N 33/24* (2013.01);
(Continued)

(58) Field of Classification Search
CPC .... G01N 33/24; G01N 1/2294; G01N 33/245; G01N 33/0031; G01N 33/004; G01N 2001/021; A01B 79/005
See application file for complete search history.

(56) References Cited

U.S. PATENT DOCUMENTS 5,639,956 A * 6/1997 Christy .................. G01V 9/007
73/19.01
2010/0241363 A1* 9/2010 Keeling ............... G01N 33/004
702/51
(Continued)

FOREIGN PATENT DOCUMENTS

DE         10240330 A1    3/2004
DE     102012008584 B3 *  6/2013  .......... G01N 1/2294
(Continued)

OTHER PUBLICATIONS

Jones D G et al.: "In Salah gas COstorage JIP: Surface gas and biological monitoring", Energy Procedia, vol. 4, 2011, pp. 3566-3573, xp028213339, ISSN: 1876-6102, Doi: 10.1016/J.EGYPRO.2011.02.285.

*Primary Examiner* — Benjamin R Schmitt
(74) *Attorney, Agent, or Firm* — Husch Blackwell LLP

(57) ABSTRACT

A system for determining soil gas attributes includes a vacuum pump configured to draw soil gasses through an air intake; a gas sensor to measure gas concentration levels in soil gasses passing through the system; a GPS unit to identify the position of the system; and a controller configured to map measurements from the at least one gas sensor relative to a position of the system. An associated method of determining sod attributes includes the steps of drawing gas samples from the soil through an air intake; transmitting the gas samples to at least one gas sensor; measuring a gas concentration in the gas sample with the at least one gas sensor; transmitting the measured gas concentration to a controller; determining a position of the air intake with a GPS unit; transmitting the position to the controller; and mapping the measured gas concentration with the position.

14 Claims, 12 Drawing Sheets

(51) Int. Cl.
  *G01N 33/24* (2006.01)
  *G01N 1/02* (2006.01)
  *G01N 33/00* (2006.01)

(52) U.S. Cl.
  CPC ..... *G01N 33/245* (2024.05); *G01N 2001/021* (2013.01); *G01N 33/0031* (2013.01); *G01N 33/004* (2013.01)

(56) References Cited

U.S. PATENT DOCUMENTS

| | | | |
|---|---|---|---|
| 2012/0024042 A1 | 2/2012 | Vass et al. | |
| 2014/0077969 A1* | 3/2014 | Vian | G08B 13/00 340/870.02 |
| 2015/0000374 A1* | 1/2015 | Romanak | G01N 33/0004 73/23.35 |

FOREIGN PATENT DOCUMENTS

| | | | |
|---|---|---|---|
| JP | 2004184105 A | 7/2004 |
| JP | 2015114319 A | 6/2015 |
| KR | 1020070055813 A | 5/2007 |
| KR | 101040073 B1 | 6/2011 |
| KR | 1020130076562 A | 7/2013 |
| KR | 20140074185 A | 6/2014 |
| WO | 0201196 A1 | 1/2002 |

\* cited by examiner

SYSTEM FOR DETECTING THE CONCENTRATION OF GASES IN SOIL

CROSS REFERENCE

This application claims the priority of, and expressly incorporates by reference herein the entire disclosure of, U.S. Provisional Patent Application No. 62/968,366, filed Jan. 31, 2020.

FIELD OF THE DISCLOSURE

The present invention relates to soil attribute measurement and evaluation and, more particularly, to systems and methods for sampling the concentration of gasses in soil and other soil attributes for plotting of those attributes within desired areas.

BACKGROUND

The composition of soil and the types and amounts of different substances within soil can impact any number of performance characteristics for utilization and evaluation of the soil. One example is identification of soil that may be more suitable to or produce higher yields from crop planting. Another example is the identification of contaminants within the soil to determine whether and how any environmental remediation should be undertaken. While soil composition can be determined at specific points with core samples, this and similar methods are extremely limited in their useful application. Therefore, there is a need for improved systems and methods to aid in the identification of soil composition in various applications.

SUMMARY OF THE DISCLOSURE

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with one aspect of the present disclosure, there is provided a system for determining soil attributes, such as gas concentration levels, that includes an air intake in fluid communication with an air movement device, for example, a vacuum pump, configured to draw soil gasses through the air intake; at least one gas sensor in fluid communication with the air intake and operable for measuring gas concentration levels in gas passing through the system; a GPS unit operable to identify the position of the system; and a controller in communication with the at least one gas sensor and the GPS unit and configured to map measurements from the at least one gas sensor relative to a system position as determined by the GPS unit.

In another aspect, there is provided a system for determining soil attributes that also includes a cleaning/recharging subsystem having a source of pressurized air; and a switchable valve in fluid communication with the pressurized air source and with the air intake; the switchable valve operable to selectively fluidly connect the pressurized air source with the air intake.

In another aspect, there is provided an associated method of determining soil attributes that includes the steps of drawing gas samples from the soil through an air intake; transmitting the gas samples to at least one gas sensor; measuring a gas concentration in the gas sample with the at least one gas sensor; transmitting the measured gas concentration to a controller; determining a position of the air intake with a GPS unit; transmitting the position to the controller; and mapping the measured gas concentration with the position.

In another aspect, there is provided a method of determining soil attributes that includes the steps of providing a system for determining soil attributes having an air intake in fluid communication with a vacuum pump configured to draw soil gasses through the air intake; at least one gas sensor in fluid communication with the air intake and operable for measuring gas concentration levels in gas passing through the system; a GPS unit operable to identify a position of the system; and a controller in communication with the at least one gas sensor and the GPS unit and configured to map measurements from the at least one gas sensor relative to a system position as determined by the GPS unit; drawing gas samples from soil through the air intake; transmitting the gas samples to the at least one gas sensor; measuring a gas concentration in the gas sample with the at least one gas sensor; transmitting the measured gas concentration to the controller; determining a position of the air intake with the GPS unit; transmitting the position to the controller; and mapping the measured gas concentration with the position.

These aspects are merely illustrative of the innumerable aspects associated with the present invention and should not be deemed as limiting in any manner. These and other aspects, features and advantages of the present invention will become apparent from the following detailed description when taken in conjunction with the referenced drawings.

BRIEF DESCRIPTION OF DRAWINGS

The foregoing summary; as well as the following detailed description will be best understood when read in conjunction with the attached drawings in which the same or similar elements are referred to by the same numerals, and where:

FIGS. 8A and 8B are a comparison of field maps of gas concentration samples produced from an embodiment of the present disclosure depicting raw data the same data after calibration based, in part, on sensor delay and expected $CO_2$ gas concentration levels.

Figure 1:
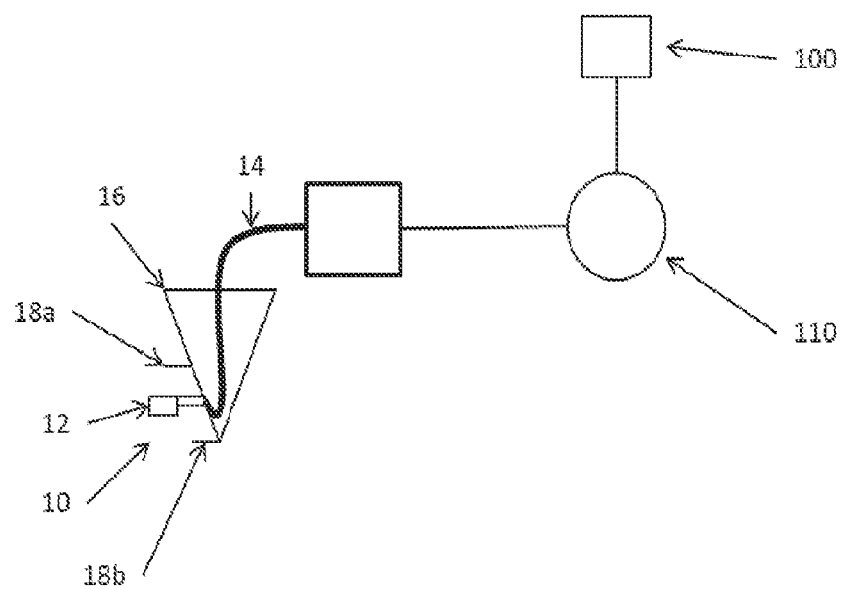
FIG. 1 is a schematic view of a gas attribute measurement system according to a first embodiment of the present disclosure.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure.

DETAILED DESCRIPTION OF THE PREFERRED EMBODIMENTS

In the following detailed description numerous specific details are set forth in order to provide a thorough understanding of the invention. However, it will be understood by those skilled in the art that the present invention may be practiced without these specific details. For example, the invention is not limited in scope to the particular type of industry application depicted in the figures. In other instances, well-known methods, procedures, and components have not been described in detail so as not to obscure the present invention. The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience; and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As used herein, the word "include," and its variants, is intended to be non-limiting; such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

It should be noted that various embodiments of the present disclosure may be incorporated directly into various farm or other soil-working/earth-moving vehicles and/or implements without limitation as to the implement type as the primary functioning of the implement does not affect the operation of the present system. Such embodiments may be installed in a permanent, fixed arrangement or in a temporary and removable arrangement. Alternately, the various components of the systems described herein may be packaged into a stand-alone unit that may be portable and readily moved from one implement or vehicle to another or carried and operated by hand, for example, in combination with a soil core sampling device. The system may utilize a soil breaking element that forms an inherent part of an implement or may be include its own soil breaking element. The latter arrangement may, for example, be advantageous in using the system with implements that do not already include soil breaking tools, such as applicator or sprayer equipment, for example. The unit may be connected with certain systems of a vehicle or implement with which it is being used, for example, the electrical system or any form of ISO or other communications bus of the vehicle or implement to supply the unit with power and connect it with other vehicle/implement components or the vehicle's or implement's on-board GPS device.

While embodiments of the present disclosure may be described in the context of soil evaluation for purposes of determining appropriate amounts of soil amendments for increased crop yields and/or to evaluate expected yields, the present disclosure is not limited to use of the system in this context. $CO_2$ levels in soil can predict soil fertility along with, alone or in combination with other present substances, soil health, productivity, and other agronomic parameters. These factors may, in turn, allow for calculation of further parameters, for example, more efficient planting populations in various areas of a field to reach a more efficient seed to yield performance.

However, the present disclosure includes application of the system in any application in which measurement of relevant attributes in an area of soil are desired. Examples may include, but are not limited to, identifying areas of soil contamination by pollutants, determining levels of such contamination to evaluate and/or maximize efficient implementation of necessary clean-up procedures, or identifying leaks from underground or above ground chemical storage facilities, industrial facilities, or other potential sources. Various attributes or soil substances that may be detected and measured may include, but are not limited to, acetaldehyde, acetic acid, acetone, acetonitrile, acetylene, acrylonitrile, alcohol, aldehydes, alkenes, alkenes, amines, ammonia, aromatics, benzene, butadiene, butane, butanol, carbon dioxide, carbon monoxide, carboxylic acids, chlorine, chlorine dioxide, chloro-compounds, chloroethane, cyclohexane, decane, diethylether, dienes, diesel fuel, esters, ethane, ethanol, ethers, ethylacetate, ethylamine, ethylene, ethylene oxide, formaldehyde, gasoline, helium, hexane, hydrogen, hydrogen sulphide, isoprene, jet fuel JP4, methane, methyl ethyl ketone, methyl methacylate, naphthalene, nitric oxide, nitrogen dioxide, octane, oxygen, paraffin, petrol, propane, propylene, styrene, sulfur dioxide, tetrahydrofuran, turpentine, VOCs, vinyl acetate, vinyl compounds, white spirits, xylem (ortho, meta, and para), relative humidity, and temperature. Various embodiments may further include a spectrophotometer, mass spectrometer, or similar devices to facilitate these analyses.

In addition, embodiments of the present disclosure may be adapted to measure concentrations of substances other than gasses, such as liquids, by, for example, substituting the air movement devices described herein with a suitable liquid pump to draw in liquid or a soil/liquid mixture into the system for delivery to a suitable sensor. It is further contemplated with the scope of the present disclosure to use embodiments of the system to evaluate other attributes of soil and the air, liquid, or other substances entrained within the soil.

Figure 2:
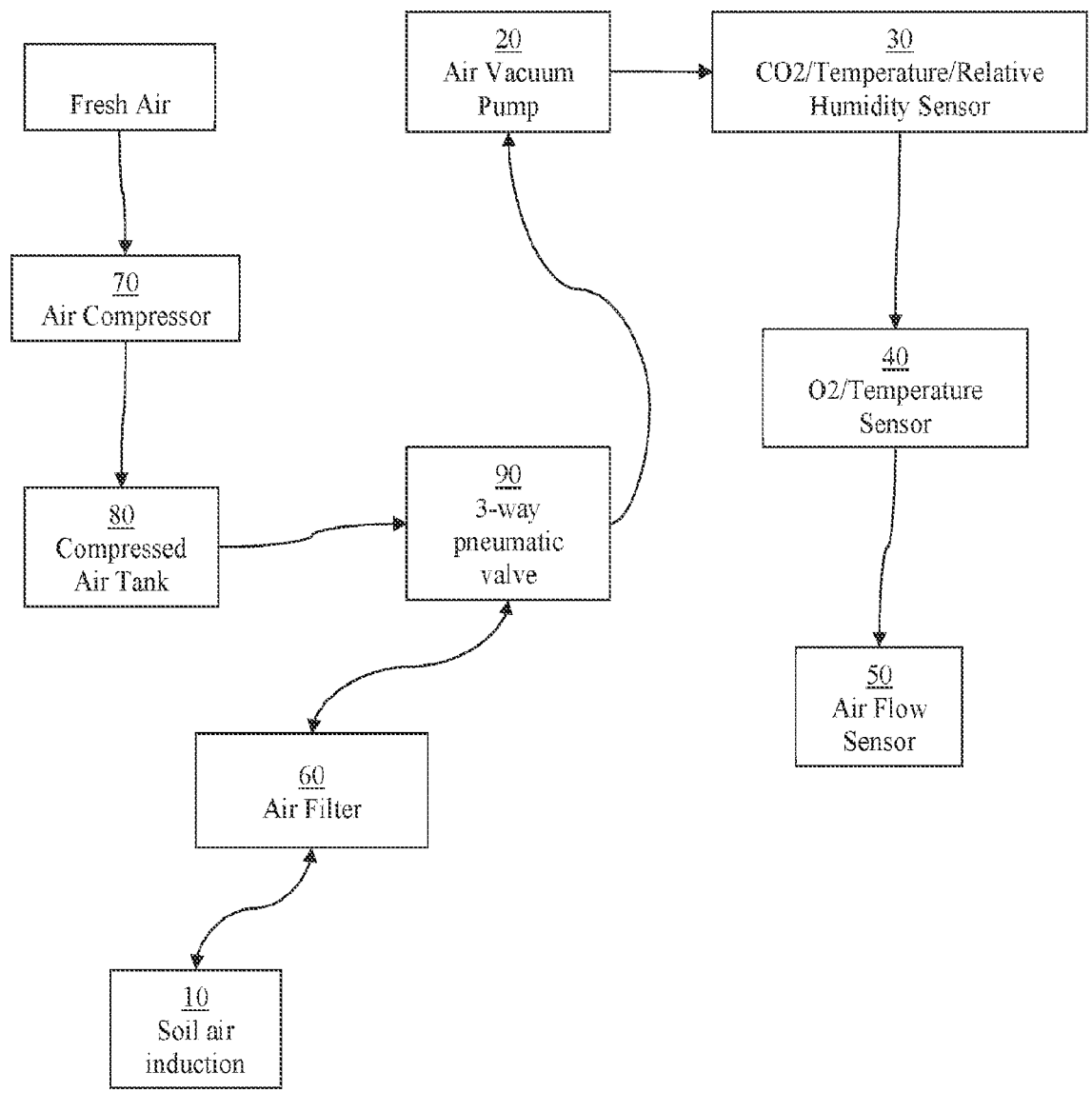
FIG. 2 is a schematic illustrating the air flow interrelationship of components of a gas attribute measurement system according to another embodiment of the present disclosure.
Figure 3:
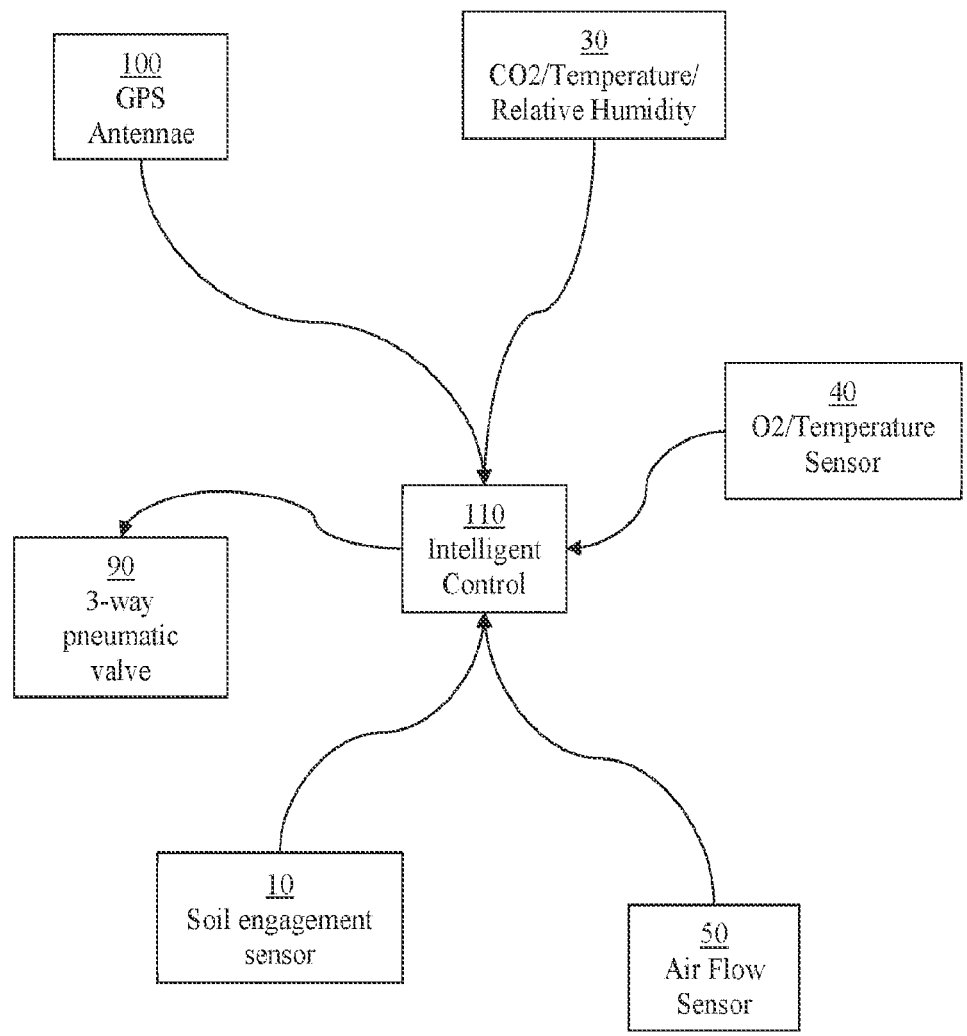
FIG. 3 is a schematic illustrating the data flow and wiring interrelationships of components of a gas attribute measurement system according to another embodiment of the present disclosure.

FIGS. 1-3 schematically illustrate embodiments of a system 5 according to the present disclosure. The system 5 may further coordinate with operation of a soil-breaking/working implement on an associated vehicle, if applicable. In such cases, certain components of the system may be appropriately positioned in relation to such implements to further facilitate operation of the system as described in more detail herein.

The specific nature of an associated implement is not critical to operation of the system, and use of an implement at all is not a requirement of the system. While one embodiment may utilize a cutting knife, positioned behind a coulter, other arrangements may also be used. More particularly, the combination of a working implement with the air intake of the system is beneficial in the sense that the operations of soil gas or other attribute measurement may take place simultaneously with plowing or other soil working applications to save time and expense. When an implement is used, it may be any common soil working or earth-moving implement, for example and not limited to soil cultivation implements (e.g., moldboard, reversible, chisel, disc, or subsoiling plows), planting machines, harvesting implements, fertilizer applicators and sprayers, tractor, bulldozers, backhoes, excavators, graders, scrapers, trenchers, or front end loaders.

The system may include an air intake 10 advantageously arranged to be placed into the soil environment being assessed and accept air emanating from that soil. More particularly, the air intake 10 is configured to facilitate rapid extraction of air from the soil in order to minimize intermixing of air extracted from the soil with atmospheric air above the soil, which can directly interfere with the accuracy of measurements taken by the system 5.

The soil air extraction process presents a number of practical challenges. One such challenge is the ability to limit the amount of soil particles extracted with the air sample. When soil particles, particularly those of larger size, are drawn in by the system 5, there exists a greater potential for damage to the sensors, as described below, employed in the system 5. Embodiments of the present disclosure address this challenge in several alternate ways, in one embodiment, the opening of an air intake inlet 12, which may be circular, rectangular, or any other suitable cross-sectional shape, is configured with a cross-sectional area that is significantly larger than an inner diameter of an air intake conduit 14 which forms a component of an outlet of the air intake 10. In a preferred embodiment, the ratio of the air intake inlet 12 to the inner diameter of the air intake conduit 14 is approximately 5:1, although other ratios may also be used without departing from the scope of the present disclosure. It has been found that employing a larger air intake inlet 12 inner diameter to air conduit 14 inner diameter facilitates lower velocities of air drawn into the air intake 10. A reduced air velocity will result in lower exerted force and turbulence in the soil, which can, in turn, reduce further soil disruption that can increase the amount of soil particulates drawn into the air intake 10.

Various embodiments of the system 5 may be provided with air intake inlets 12 of different configurations, for example, pipe sections, nozzles, pipe fittings, and similar items. The desired characteristics for the air intake inlet 12 may include an open end having the cross-sectional size measurements described above and an opposite end configured to securely and sealingly mate with the air conduit 14 in a largely air-tight manner to facilitate effective transfer of air collected from the soil into the system 5 for measurement.

The air conduit 14 may include either rigid or flexible piping or hose that is largely air-tight or sufficiently air-impermeable to minimize air transfer through the walls of the air conduit 14. The inner diameter of the air conduit 14 may be in accordance with the cross-sectional area ratios described above. The outer diameter of the air conduit 14 may be of essentially any dimension with the understanding that particular applications may impose exterior size requirements on the conduit 14 to facilitate installation. While using flexible tubing in the air conduit 14 provides for ease of installation due to its ability to more readily be routed through and/or around various obstacles, rigid piping, while potentially requiring a more involved installation process, may provide an advantage in durability and resulting lifespan, particularly in embodiments of the system that may be permanently installed in a particular vehicle or implement.

The air intake 10 may be associated with a soil working or breaking implement 16. The soil working/breaking implement 16 may be incorporated with the air intake 10 itself, or an existing implement, such as may be found on a tiller, planter, or cultivator, may be used by appropriately locating the air intake 10 relative to the implement. The soil working/breaking implement 16 may be configured to create a small row or trench within which the air intake 10 travels. In one embodiment, the soil working/breaking implement 16 may create a row or trench having a depth of approximately 2" to 4" as a row or trench of that depth provides suitable exposure of the air intake 10 to the soil while keeping soil disturbance and resulting soil particulates in the air to a reasonable level, although other embodiments may be employed to measure at other soil depths. In a preferred embodiment, the air intake inlet 12 is positioned rearward, relative to the direction of travel of the vehicle/implement, of the soil work/breaking implement 16. The air intake 10 may further include a soil engagement sensor, for example, but not limited, a whisker switch, proximity switch, or pressure switch, to allow the system 5 to identify when the air intake is in the soil and when it is raised out of the soil. This component is particularly advantageous in combination with the data correction/calibration methods described herein.

In another embodiment, the soil working/breaking implement 16 further may include one or more spurs 18. The spurs are associated with the trailing side of the soil working/breaking implement 16. The spurs may include a top spur 18a located above the air intake inlet 12 and/or a bottom spur 18b located below the air intake inlet 12. If present, the top spur 18a prevents soil displaced by the leading edge of the soil working/breaking implement 16 from immediately falling back into the trench and on or into the air intake inlet 12. The top spur 18a may also serve as a form of barrier that at least partially shields the air intake inlet 12 from atmospheric air. The bottom spur 18b, if present, may help prevent plugging of the air intake inlet 12 during initial contact with the soil and/or fouling of the air intake inlet 12 from the recently disturbed soil. The spurs 18 may be horizontally or vertically oriented.

An air vacuum pump 20 or other fluid movement mechanism in fluid communication with the air intake 10 may also be provided. The air vacuum pump 20 operates to draw in air through the air intake 10. In various embodiments, the air vacuum pump 20 may be connected with the air intake 10 by the air intake conduit 14. In an exemplary, non-limiting embodiment, the air vacuum pump 20 is a high suction diaphragm pump producing a flow rate or suction capacity of approximately 8 L/min with a pressure range of approximately 500 to 8,000 mmHG. It is preferred that the air vacuum pump 20 may be configured to maintain a high air velocity and positive pressure after the pump 20. In another embodiment, two pumps operating in series may be used instead of a single pump. Other pumps or other air movement devices may be utilized in alternate embodiments in accordance with the present disclosure.

The air drawn into the system 5 through the air intake 10 by the air vacuum pump 20 is transferred to one or more sensors that are in fluid communication with those system components. Where multiple sensors are provided, they may be connected in series or parallel in the system 5. In one embodiment, the first such sensor is a $CO_2$ sensor 30 that detects and measures the amount of $CO_2$ that is present in the air drawn into the system 5 from the soil. The $CO_2$ sensor 30 may preferably be calibrated to measure atmospheric air in the range of 0 ppm to 10,000 ppm (0% to 1%) of $CO_2$. The $CO_2$ sensor may be a nondispersive infrared sensor. One example of a suitable $CO_2$ sensor may be the K30 10,000 ppm $CO_2$ Sensor from CO2Meter.com. In some embodiments, the $CO_2$ sensor 30 may further be a combination $CO_2$, temperature, and relative humidity sensor to measure those additional soil attributes. One example of such a sensor may be the CozIR®—A 10,000 ppm $CO_2$ +RH/T Sensor from CO2Meter.com. Another example of such a sensor may be the Grove SCD30 $CO_2$ & Temperature & Humidity Sensor. In some embodiments, the $CO_2$ sensor 30 may be supplemented with an O2 sensor or a combination $O_2$ and temperature sensor 40. In a preferred such embodiment, the $CO_2$ and $O_2$ sensors 30, 40 are configured in series in the system 5, with the $CO_2$ sensor 30 positioned ahead of the $O_2$ sensor 40.

In some embodiments, an air flow sensor 50 may incorporated into the system 5, preferably behind the sensors 30 and/or 40 in the direction of flow. The air flow sensor 50 measures the rate of flow of air through the system 5 and may trigger an alarm or other notification if the air flow rate drops below a predetermined threshold, which may indicate a plugged condition, for example, if the air intake or other components are so contaminated with soil particulates that air is no longer flowing freely therethrough, or a malfunction of the vacuum pump 20 or other components in the system 5, which in any of these cases would result in inaccurate measurements or no measurements being taken by the system 5.

As noted previously, contamination of various components of the system 5 by soil particulates is a significant challenge. While the configuration of the air intake 10 described herein is intended to reduce soil particulate contamination and plugging, some embodiments may further include an air filter 60 to protect, in particular, the sensors 30 and/or 40, which are particularly susceptible to damage from such particulate matter, but also the air vacuum pump 20 as it is not possible to preemptively eliminate all such contamination from the system 5 entirely with any configuration of the air intake 10. The air filter 60 is preferably positioned in the system 5 ahead of the air vacuum pump 20 and sensors 30, 40 in the direction of air flow. In a preferred embodiment, the air filter 60 is relatively thin, for example, a 0.023μ filter, A further preferred version of such a filter includes tube fitting barbs on both its inlet and outlet sides to facilitate connection into the system 5. Filtering of the system 5 may be facilitated by providing two air filters 60, preferably configured in parallel in the system 5. The use of two filters in parallel may result in reduced air velocity losses across the filters compared to the degree of such efficiency losses across a single filter.

As those of skill in the art will recognize, after a period of operation, the air filter(s) 60, and potentially other system components, will eventually become clogged or fouled with soil particles. It is possible to simply shut the system down and manually remove and clean or replace the air filter(s) 60 and/or other system components. However, this requires significant system downtime and can be a significant obstacle to efficient use of the system if such stoppages are required during operation. Therefore, in a preferred embodiment, the system 5 includes a sub-system configured to allow for self-cleaning or regeneration of the system, thereby reducing system downtime and maintenance. In a preferred method of operation, the self-cleaning/regeneration steps are conducted when the apparatus reaches the end of a field row and during the process of turning around to the next row. Advantageously, this allows the system to conduct these steps while the implement and air intake 12 are raised out of the soil and within a limited space and during continued movement of the implement and system 5, thereby minimizing any interruption to the process of obtaining soil gas measurements and/or operation of the implement.

An air compressor 70 and/or compressed air tank 80 may be provided in the system 5. In some embodiments, the air compressor 70 provides source of compressed air. The compressed air produced by the air compressor 70 may be stored in the tank 80 or supplied directly to the remaining components of the system 5 as described below. In the case of embodiments utilizing a tank 80, the air compressor 70 may be controlled to operate at a frequency and duration to maintain the amount of compressed air in the tank 80 at a desired threshold volume and pressure. Sensors associated with the tank 80 that monitor the pressure within the tank 80 may send a sensor signal to a controller, t example, the controller 110 described below, which in turn initiates operation of the air compressor 70. Alternately, if no tank 80 is utilized, the controller may instead initiate operation of the air compressor 70 whenever a cleaning/regeneration cycle is initiated.

As described above, during normal operation of the system 5, air is drawn in to the system 5 through the air intake 10 and air filter 60 and to the $CO_2$ 30 and $O_2$ 40 or other sensors and air flow sensor 50. During cleaning/regeneration cycles, air may flow in the opposite direction through the air filter 60 and out air intake 10 in order to force or blow contaminants back out of those components. Therefore, it is advantageous to be able to control the direction of air flow through those components, in preferred embodiments, this may be accomplished through the use of a diverter valve 90 that is in-line with the vacuum pump 20 and air intake 10 and filter 60 and also in fluid communication with the source of compressed air, whether that be the air compressor 70 directly or the compressed air tank 80. In one embodiment, the diverter valve 90 may include a 3-way, solenoid, pneumatic valve 92. The solenoid valve 92 may have a normal position allowing for air flow from the air intake 10 and filter 60 to the vacuum pump 20 and an energized position that closes the air flow path between the vacuum pump 20 and air intake 10 and filter 60 and opens an air flow path from the compressed air source 70 and/or 80 to the air filter 60 and air intake 10. In the latter position, compressed air may be forced back through the air filter 60 and air intake 10, thereby blowing debris and contaminants out of those components resulting in cleaning/regeneration of the filter 60 and intake 10.

In a preferred embodiment, the diverter valve 90 may be configured to be controlled by the controller 110 or another device. In particular, in embodiments employing a 3-way solenoid valve, the controller 110 or other device may supply a flow of electricity to the solenoid 92 causing the solenoid 92 to shift from its normal position to its energized position in which compressed air may flow from the compressed air source 70/80 to the filter 60 and intake 10 to facilitate a cleaning/regeneration cycle. When the cycle is complete, which may be determined based upon readings from the air flow sensor 50 and/or a timer, the controller 110 or other device discontinues the flow of electricity to the solenoid 92, thereby allowing it to return to its normal position in which air may be drawn through the intake 10 and filter 60 by the vacuum pump 20. Note that the above described operation of the solenoid 92 may be reversed such that the normal position of the solenoid allows air flow between the intake 10 and filter 60 and the compressed air source and the energized position allows air flow between the vacuum pump and the intake 10 and filter 60. Further, the diverter valve 90 may be positioned elsewhere in the system 5 relative to the vacuum pump 20, $CO_2$ sensor 30, $O_2$ sensor 40, and air flow sensor 50.

The controller 110 may reside with the other components of the system 5 or be located remotely from those components, in which case the controller 110 may communicate with the other system components directly or through an associated vehicle's or implement's communication network.

In a particularly preferred embodiment, the system 5 further incorporates a GPS unit 100. The GPS unit 100 monitors the global position of the system 5 and/or vehicle on which it is mounted as it moves around a field or other space being measured. In alternate embodiments, the system 5 may make use of an existing GPS unit associated with the implement and/or vehicle. The connection between the system 5 and the remote GPS unit may be direct or through an existing communication network, e.g. ISO or other communication bus, associated with the implement and/or vehicle.

The GPS unit 100 may communicate with the controller 110 and may transmit location data to the controller 110. Advantageously, this arrangement allows the controller 110 to coordinate readings from at least the $CO_2$ 30 and $O_2$ 40 or other sensors with the location data provided by the GPS unit 100. This coordinated data allows the controller 110, or a separate computer to which the controller's data may be downloaded during or after operation, to produce a data map, such as that shown in FIGS. 5-8, that illustrates the $CO_2$ and $O_2$, or other gasses, levels at specific locations throughout the field. These data maps may provide more accurate information of where within a field higher $CO_2$ levels exist.

As noted above, the controller 110 may be in communication with various other components incorporated into the system 5, such as with the air compressor 70, compressed air tank 80, diverter valve 90, and/or sensors associated with the tank 80, $CO_2$ sensor 30, $O_2$ sensor 40, air flow sensor 50, vacuum pump 20, and GPS unit 100, in order to control and coordinate operation of these components as described above. FIG. 3 presents an exemplary data flow/wiring schematic for an embodiment of the present disclosure. The controller 110 may initiate data reading by directing electrical power to the vacuum pump 20 to initiate air flow into the system 5. At the same time, it may activate the various sensors 30, 40, 50 and receive data from those sensors while it also activates and receives data from the GPS unit 100.

In one particular aspect, the controller 110 may receive a signal from the air flow sensor 50 to monitor for any reduction or disruption in air flow through the system 5. In response to a reduction in air flow, the controller 110 may initiate a cleaning/regeneration cycle by: (a) interrupting the supply of electrical power to the vacuum pump 20 to suspend its operation, (b) sending (or interrupting the supply of) electrical power to the solenoid valve 92 to redirect air flow to the path connecting the air compressor 70 and/or compressed air tank 80 with the air filter 60 and air intake 10, and (c) supplying electrical power to the air compressor 70 to begin operation, if necessary at that time, to supply compressed air to the air filter 60 and air intake 10. Further, the controller 110 may monitor the sensors associated with the compressed air tank 80 and control operation of the air compressor 70 accordingly to maintain a desired pressure within the tank. The controller 110 may maintain the cleaning/regeneration cycle for a predetermined amount of time or upon receiving optimal readings form the air flow sensor 50 before operating the diverter valve 90 to return the system 5 to its normal operating state until the air flow sensor 50 again detects a reduction in air flow in the system. In alternate embodiments, the vacuum pump 20 and compressor 70 may operate continuously. In that case, the controller 110 would simply activate the solenoid valve 92 to redirect air flow in order to start and stop a cleaning/regeneration cycle. This manner of operation may result in faster transitions between normal operation and cleaning/regeneration.

While the system of the present disclosure is well suited to addressing the technical problem described herein, it has been found that embodiments of a data sampling and smoothing method may further enhance the accuracy of the system when incorporated into the data collection and analysis logic of the system. The referenced method may provide a better statistical fit from the collected data and better account for expected variability in measurement accuracy due to unavoidable changes in sampling collection during operation of the system. More particularly, the method may allow for the use gas sensors, for example, CO2 and O2 sensors, with lower than ideal sensitivity and repeatability capabilities. For example, because variations of 20 ppm in detected levels of some gasses can be significant, sensors with a repeatability of +/−50 ppm, resulting in potential measurement variation of up to 100 ppm, might otherwise produce less than optimal results. In some embodiments, accuracy may be enhances through the use of redundant sensors whose readings are averaged to enhance accuracy and/or provide a means of quality control of the sensors' performance. Further, the data points are obviously affected when the air intake 10 is raised to allow vehicle to make turns within the measured field.

While the traditional means for fitting data points to a curve is to average multiple data points together, it has been found that this method results in significantly less accurate data curves as intervening values are overly flattened, thereby eliminating valuable data. This is particularly true with respect to the portions of the data associated with turns of the vehicle when the system is not in direct contact with the soil and, thus, taking readings from atmospheric air rather than soil gas.

Figure 4:
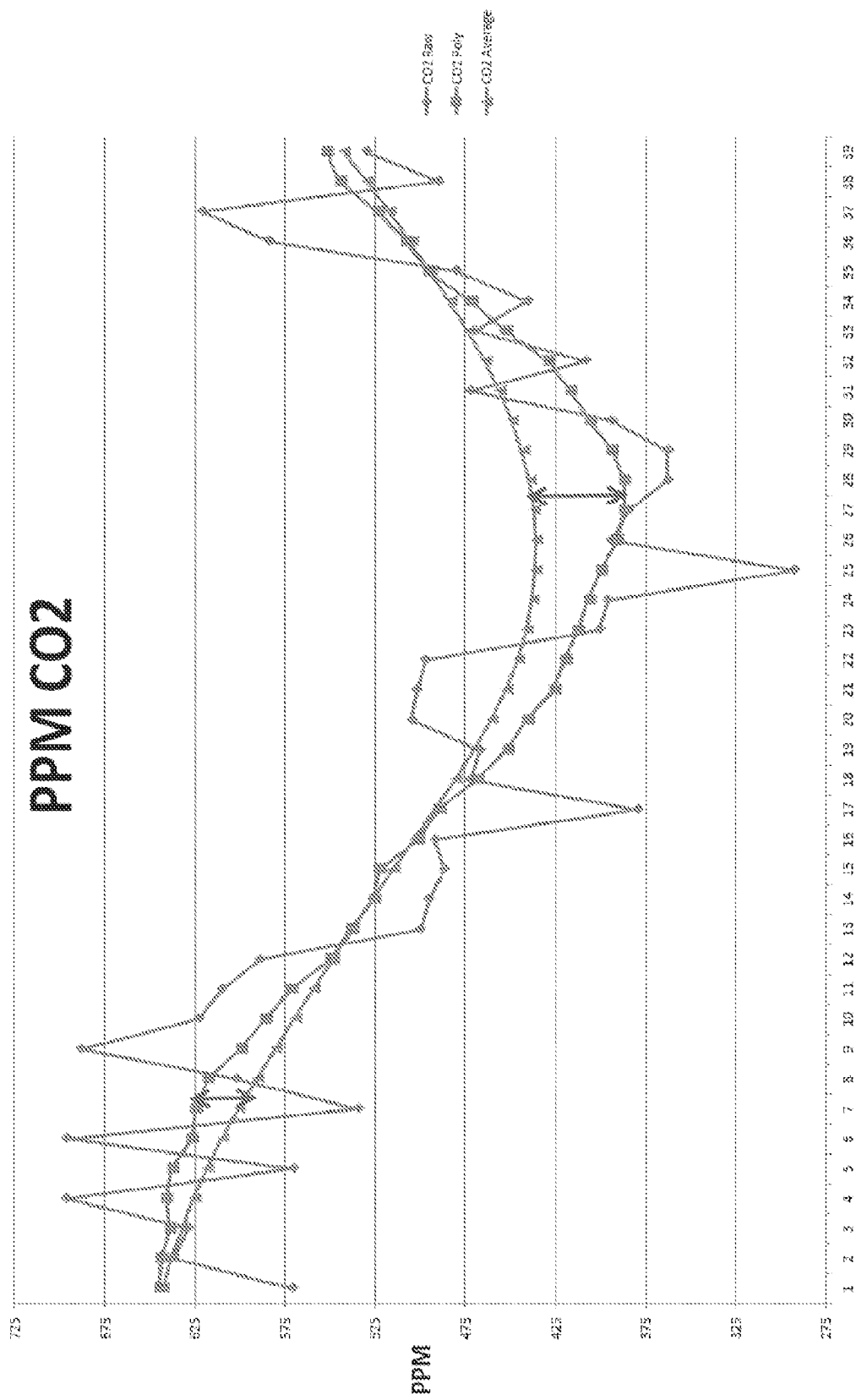
FIG. 4 a graph plotting raw data points produced from an embodiment of the present disclosure, a curve produced by averaging the raw data points, and a polynomial curve produced from the raw data points.
Figure 5A:
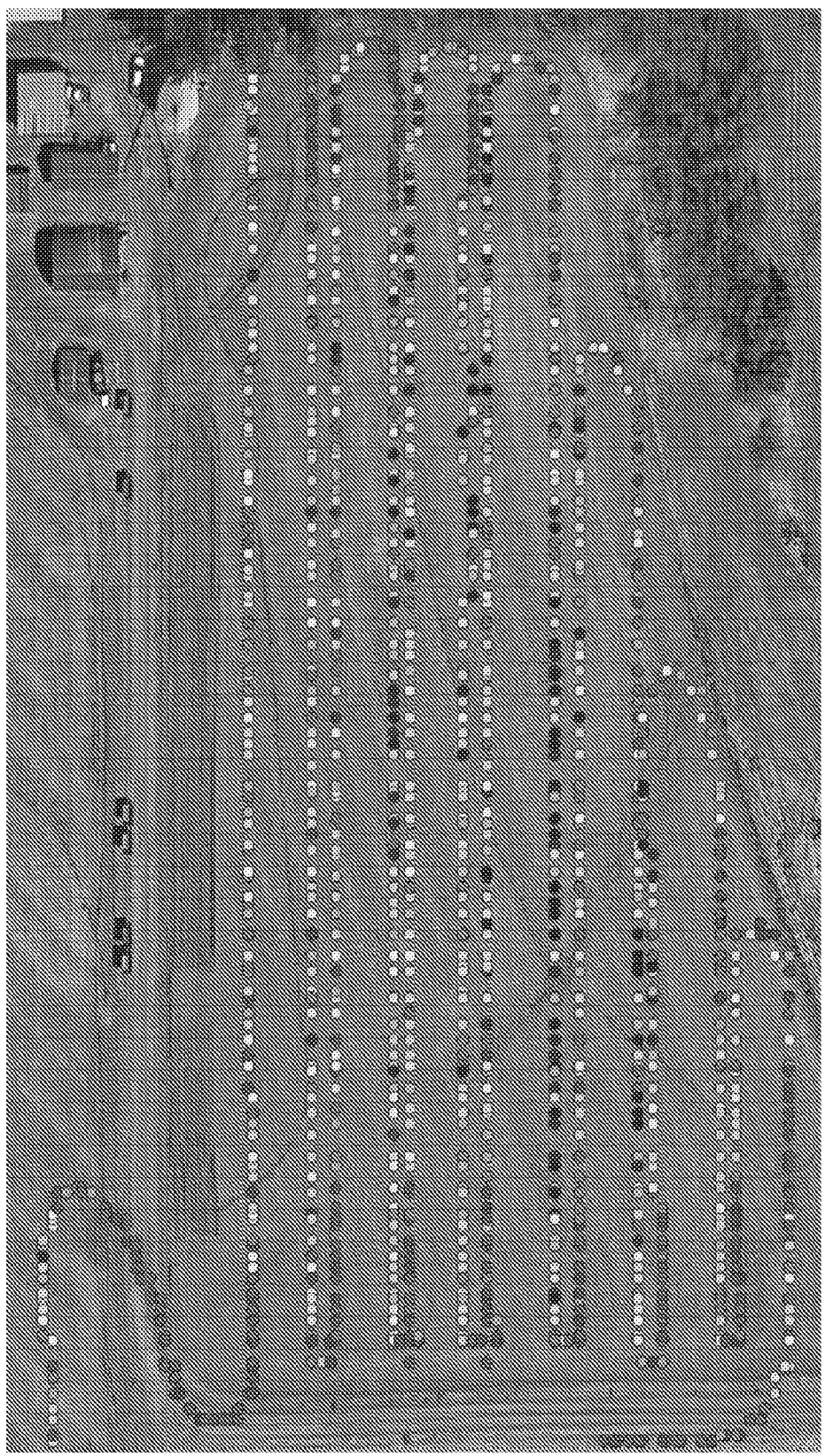
FIGS. 5A and 5B are a comparison of field maps of gas concentration samples produced from an embodiment of the present disclosure depicting raw data and post-smoothing data.
Figure 5B:
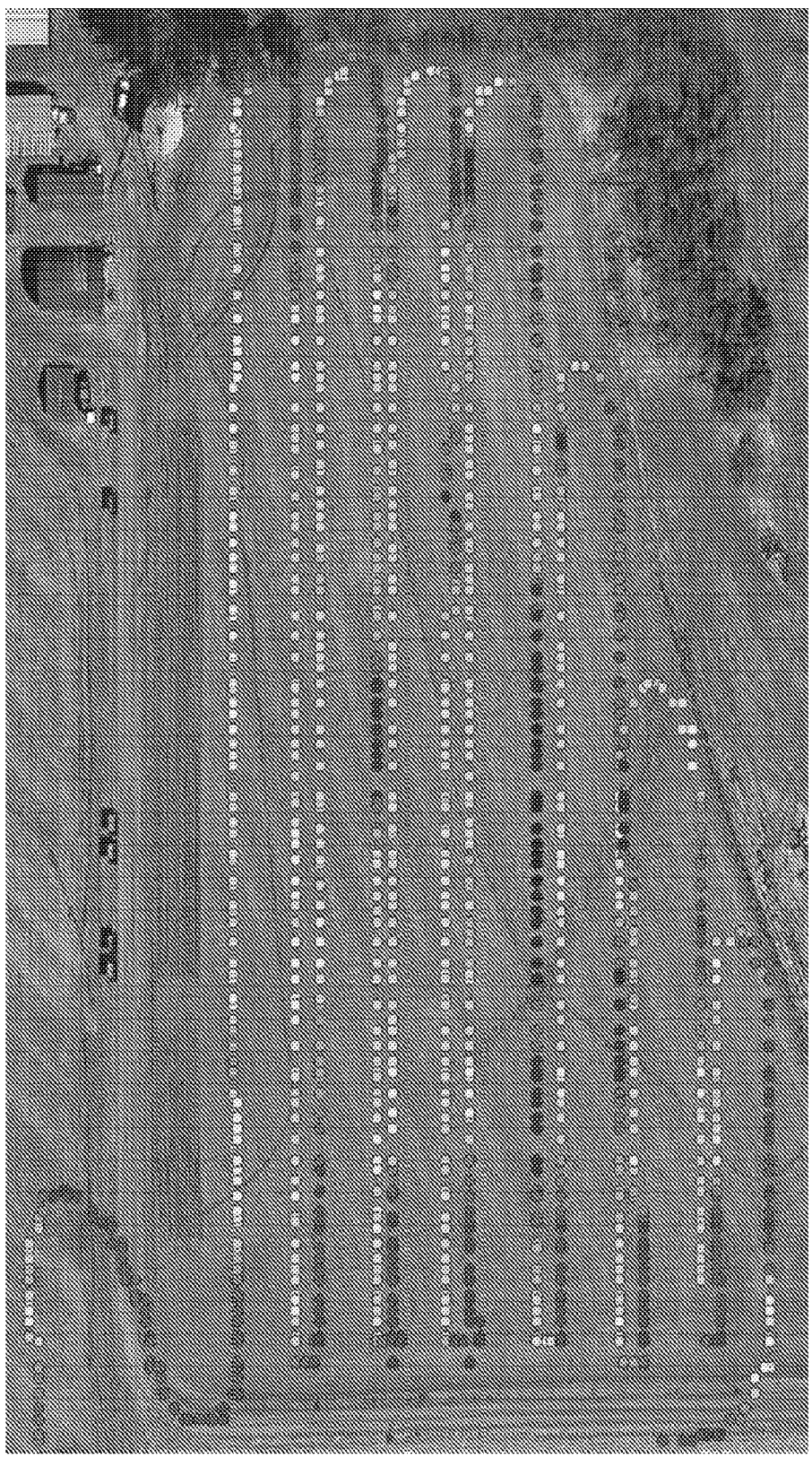

Instead, it is preferred to produce a polynomial output from calculating the polynomial curve from the collected data points. The difference in the result produced by this method versus the traditional methodology is illustrated in FIGS. 4 and 5A and 5B, which also provides the raw data points and identifies exemplary sections where the two methods produce meaningfully disparate information. FIG. 5A illustrates pre-correction data while FIG. 5B illustrates post-correction data. More particularly, it has been found that this methodology more accurately reflects the actual variations in gas concentration levels from sample to sample. However, with respect to CO2 sensors, polynomial averaging is not as necessary with higher quality sensors.

Figure 6A:
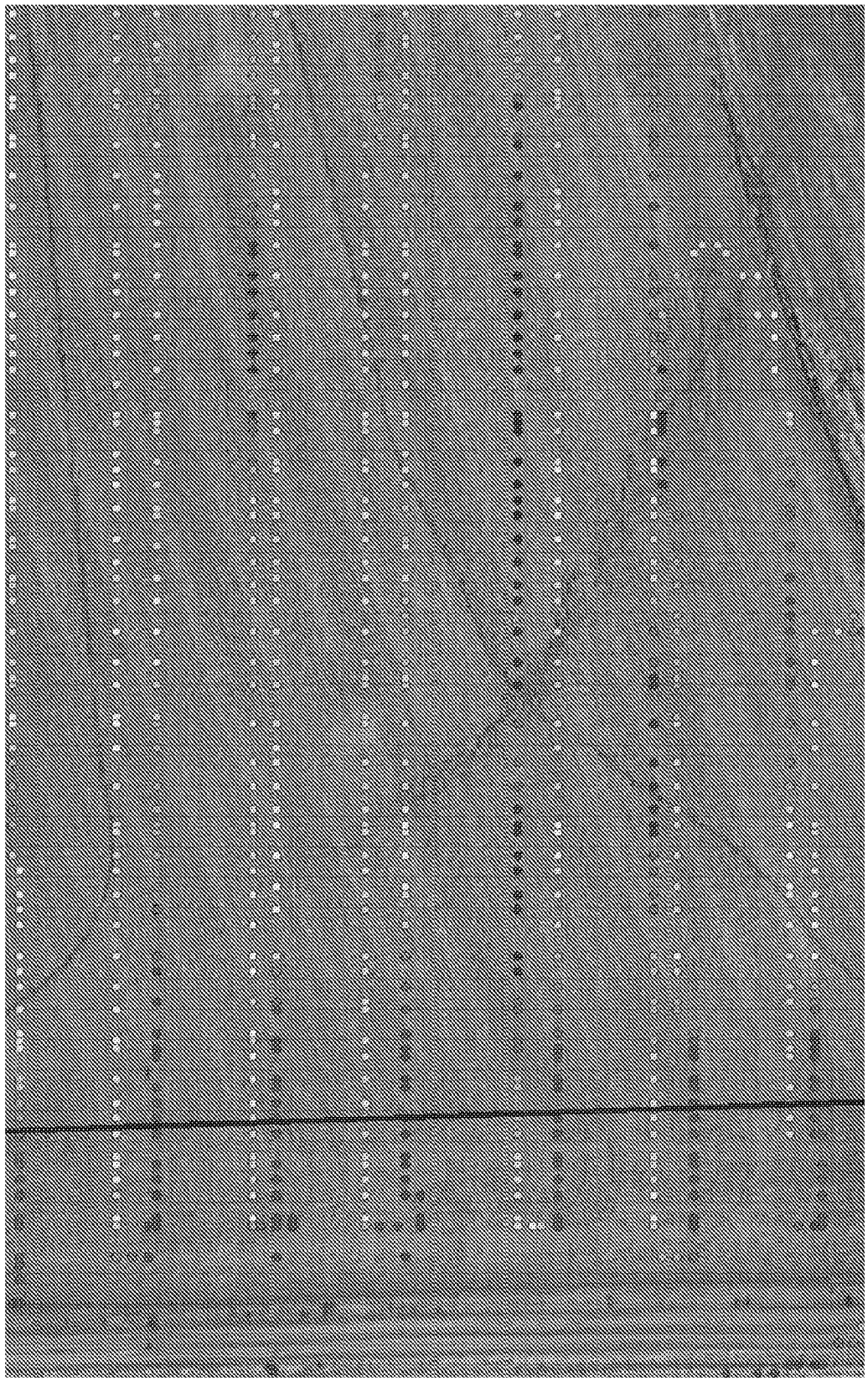
FIGS. 6A and 6B are a comparison of field maps of gas concentration samples produced from an embodiment of the present disclosure depicting raw data the same data after correction based, in part, on calculating measurement delay.
Figure 6B:
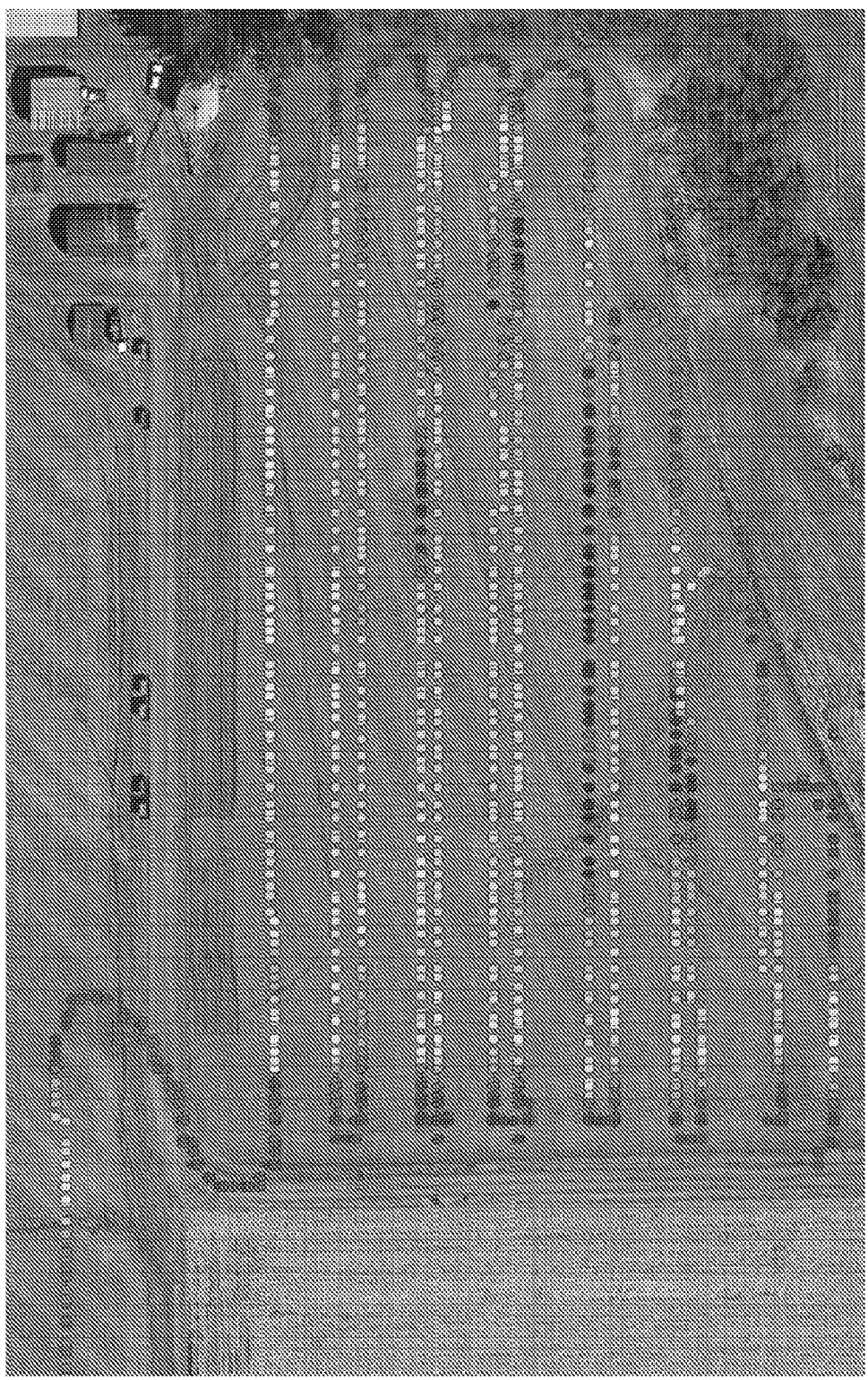

FIGS. 6A and 6B illustrate the result of a second data correction step that may be incorporated into aspects of the present disclosure, with FIG. 6A illustrating pre-correction data and FIG. 6B illustrating post-correction data. It is noted that there may be some degree of delay in concentration readings taken by the system relative to identification of the position of the system as determined by the GPS unit. The delay may result from the time it takes for gas samples to pass from the air intake to the sensors. This delay may result in skewing of the data points relative to where the sampling associated with a given data point actually occurred. According to this aspect, this delay may be determined and utilized to correct the data points such that their positional accuracy is retained.

More particularly, the system identifies where the air intake is lifted out of the soil to allow the implement to turn and where it is lowered back into the soil. Further, the system combines this information with the expected gas concentration levels present in atmosphere—versus soil—to identify the amount of shifting in the data points resulting from the measurement delay, which in turn corresponds to the shift that should be made to the data points to more accurately reflect their relative positioning within the field. More particularly, the time period during which the air intake is out of the soil, drawing in atmospheric air rather than soil gasses, is determined. The gas concentration levels obtained during that time period plus a period of time thereafter are averaged, and the time period having the lowest average gas concentration represents the delay utilized in the system's calculations. This calculation results in the sensor readings being adjusted to correspond to the determined GPS location minus the determined time delay. Further, the system may account for delay arising from the positioning of the GPS unit 100 relative to the air intake 10 where the GPS unit 100 is not immediately adjacent to the air intake 10, for example, when the GPS unit of an implement or a carrying unit, e.g., a tractor, combine, bulldozer, etc., is used, which may be a number of feet away from the air intake 10.

As a non-limiting example, if the time period during which the air intake is raised out of the soil is 30 seconds, readings taken from that time period following raising of the air intake is average. This averaging is continued for at least 45 seconds. If the sensor were to operate instantaneously, the lowest averaged value would occur at approximately 15 seconds, the midpoint in time between the raising and lowering of the air intake. However, if the lowest averaged value is instead measured at 24 seconds after the air intake is raised, then the sensor delay would be calculated as 24 seconds minus the control value of 15 seconds for a delay of 9 seconds.

In FIG. 6A, the vertical black line represents the approximate point at which the implement raises and lowers the air intake to accommodate a turn. The data points shown indicate the corresponding measurement delay. Once the above described corrective step is taken, the adjusted data map more accurately reflects the positioning of the data points relative to the raising and lowering of the air intake.

Figure 7A:
FIGS. 7A and 7B are a comparison of field maps of gas concentration samples produced from an embodiment of the present disclosure depicting raw data the same data after calibration based, in part, on air velocity through the system and expected $CO_2$ gas concentration levels.
Figure 7B:
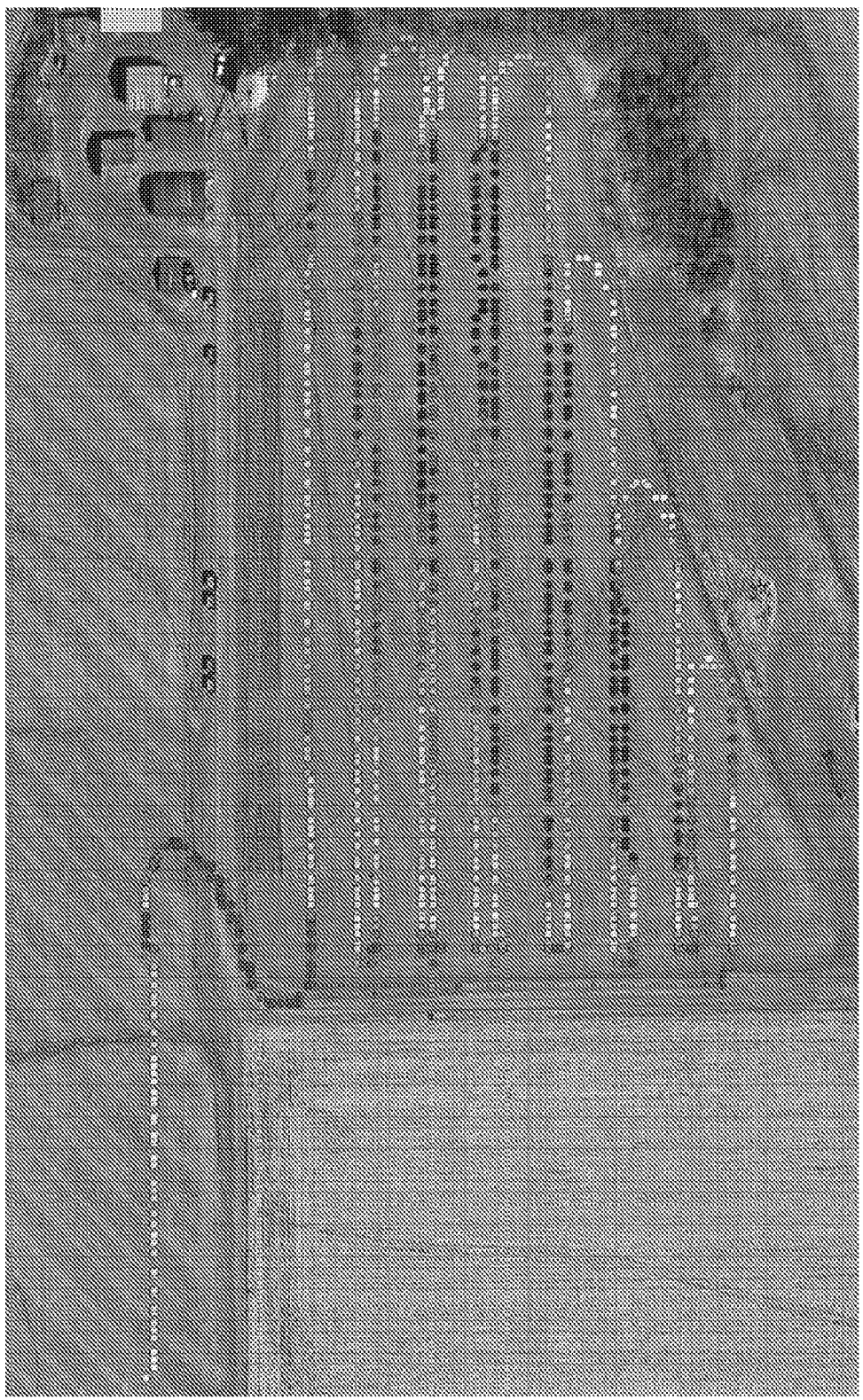

FIGS. 7A and 7B illustrate an embodiment of a method of calibrating the sensor data of the system, with FIG. 7A illustrating pre-calibration data and FIG. 7B illustrating post-calibration data. This step again uses expected atmospheric gas concentrations and determination of when the air intake is raised out of the soil and, therefore taking atmospheric rather than soil gasses, but, in this case, combines that information with measurements of the velocity of air passing through the system. More particularly, the system calculates from the air velocity in the system when the measured concentration values should reach the expected atmospheric gas concentration. The difference between this expected time to reach the expected gas concentration and the actual time taken to flush soil gas levels from the system to reach the expected atmospheric gas concentration represents a correction factor that the system subsequently uses to calibrate sensor readings. Again, the two data maps represent, first, data points taken without this calibration step and, second, those same data points after the calibration step.

Figure 8A:

FIGS. 8A and 8B illustrate a second embodiment of calibrating the sensor data of the system, with FIG. 8A illustrating pre-calibration data and FIG. 8B illustrating post-calibration data. The illustrated embodiment uses a calibration step that relies upon $O_2$ levels. However, it should be noted that other gas levels, for example hut not limited to $CO_2$ or $N_2$, may also be measured and utilized in this calibration method, Measurements of some soil gasses, for example, $O_2$, levels have a tendency to gradually drift up and down, departing from the actual concentration levels relative to sample location and missing subtle variations in actual soil concentration levels, particularly with the use of less expensive sensors. More accurate sensors are available but are still subject to this effect to a lesser degree but at significant cost. The system again determines at what points the air intake is raised out of the soil, where it begins sampling atmospheric rather than soil gas levels. During the period of time between when the air intake is raised and then lowered, there is a determinable linear change in measured gas levels, first rising then lowering, that the system then uses that information to calibrate the readings taken by the sensor over the course of the remainder of the data map. Again, the two data maps represent, first, data points taken without this calibration step and, second, those same data points after the calibration step.

With respect to the foregoing calibration embodiments, it should be noted that where expected atmospheric air concentrations are utilized, a sample of air containing the expected gas concentrations, for example, a container with such a sample, may be incorporated into the system directly rather than taking readings from atmosphere.

Figure 9B:

FIG. 9 illustrates a graphing result from another embodiment of the present disclosure. Typically, yield data is recorded and analyzed as a series of points. These yield points comprise a latitude and longitude to identify a geographical location and correspond that location with a single yield value. Using these yield points tends to oversimplify the yield data however.

Instead, a polygon may be utilized with the measured yield data to provide higher resolution data graphing. The associated polygon represents an approximate footprint of the soil from which measured yield data was taken. FIG. 9 illustrates an exemplary mapping using polygon based yield data. In this example, the polygon or footprint is generally arched in shape, with the arches pointing in the direction of travel of the vehicle.

The polygon based yield data is calculated from the ground speed of the vehicle, the total width of the implement be used on the vehicle, for example, a grain harvesting header, the feeder house width—(the width of the intake throat of a combine), the header inward speed, and the previous harvested area. These metrics determine both the area and shape of the associated polygon, and, therefore, these characteristics may change. As an example, if the vehicle velocity increases, the degree of the arch in the polygon increases. Decreasing velocity would result in a flatter arch.

While in a preferred embodiment, all of the foregoing correction and calibration steps may be utilized in the system, it is contemplated within the scope of the present disclosure that these steps may be utilized separately or in combination with one another.

It is also noted that the systems and methods of the present disclosure, while described in the context of possible agricultural uses, have applicability in other applications for which determination of soil gas levels, including levels of gasses other than $CO_2$ or $O_2$ of various types with an appropriate gas sensor, may be useful. In the described embodiments, $CO_2$ or other gas concentrations may be used to calculate soil fertility, yield expectations and/or recommended nitrogen, phosphorus, or other fertilizer application. The data may further allow more efficient seed planting population in various areas to maximize seed to yield efficiency. Further, the systems and methods described herein may be utilized for soil testing at a variety of soil depths with minor modification of the air intake—and use of a suitable implement to position the air intake at the desired soil depth.

The preferred embodiments of the invention have been described above to explain the principles of the invention and its practical application to thereby enable others skilled in the art to utilize the invention in the best mode known to the inventors. However, as various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by the above-described exemplary embodiment, but should be defined only in accordance with the following claims appended hereto and their equivalents.

The invention claimed is:

1. A system for determining soil attributes, comprising:
   an air intake mounted on a soil-working implement of an associated vehicle and in fluid communication with a vacuum pump mounted on said associated vehicle, said air intake and said vacuum pump configured to continuously draw soil gasses from soil through said air intake during movement of said associated vehicle;
   at least one gas sensor in fluid communication with said air intake and operable for continuously receiving soil gasses from said air intake and measuring gas concentration levels in said soil gasses received from said air intake during movement of said associated vehicle;
   a GPS unit operable to identify a position of said system during movement of said associated vehicle and while said at least one gas sensor receives soil gasses from said air intake and measures gas concentration levels; and
   a controller in communication with said at least one gas sensor and said GPS unit and configured to map measurements from said at least one gas sensor relative to a system position as determined by said GPS unit.

2. The system for determining soil attributes as set forth in claim 1, wherein said at least one gas sensor is at least one of a $CO_2$ sensor, $O_2$ sensor, or $NH_4$ sensor.

3. The system for determining soil attributes as set forth in claim 1, further comprising at least a second gas sensor.

4. The system for determining soil attributes as set forth in claim 1, further comprising at least one of a spectrophotometer or a mass spectrometer.

5. The system for determining soil attributes as set forth in claim 1, further comprising a temperature sensor.

6. The system for determining soil attributes as set forth in claim 1, further comprising a relative humidity sensor.

7. The system for determining soil attributes as set forth in claim 1, further comprising a cleaning/recharging subsystem comprising:
   a source of pressurized air;
   a switchable valve in fluid communication with said pressurized air source and with said air intake; said switchable valve operable to selectively fluidly connect said pressurized air source with said air intake.

8. A method of determining soil attributes, comprising the steps of:
   continuously drawing soil gasses from soil through an air intake with a vacuum pump during movement of an associated vehicle having a soil-working implement on which said air intake is mounted;
   continuously transmitting said soil gasses to at least one gas sensor during movement of said associated vehicle;
   measuring a gas concentration in said soil gasses with said at least one gas sensor;
   transmitting said measured gas concentration to a controller;
   determining a position of said air intake with a GPS unit during movement of said air intake with said associated vehicle;

transmitting said position to said controller; and
mapping said measured gas concentration with said position.

9. The method of determining soil attributes as set forth in claim 8, further comprising the steps of:
repeating said steps of measuring said gas concentration, determining said position, transmitting said position to said controller, and mapping said measured gas concentration with said position to produce a series of geographically located gas concentration data points; and
producing a polynomial output from calculating a polynomial curve from said series of geographically located gas concentration data points.

10. The method of determining soil attributes as set forth in claim 8, further comprising the steps of:
repeating said steps of measuring said gas concentration, determining said position, transmitting said position to said controller, and mapping said measured gas concentration with said position to produce a series of geographically located gas concentration data points;
determining a first location at which said air intake is lifted out of the soil and a second location at which said air intake is lowered back into the soil;
measuring a first gas concentration level at said first location and a second gas concentration level at said second location;
comparing an expected gas concentration level with said first and second measured gas concentration levels; and
adjusting said series of geographically located gas concentration data points based on a difference between said expected gas concentration level and said measured gas concentration levels.

11. The method of determining soil attributes as set forth in claim 8, further comprising the steps of:
repeating said steps of measuring said gas concentration, determining said position, transmitting said position to said controller, and mapping said measured gas concentration with said position to produce a series of geographically located gas concentration data points;
determining a first location at which said air intake is lifted out of the soil and a second location at which said air intake is lowered back into the soil;
measuring a velocity of gas passing from said air intake to said at least one gas sensor;
determining from said first and second locations and said measured gas velocity an expected period of time for said measured gas concentration to reach an expected gas concentration level;
measuring an actual period of time for which said measured gas concentration reaches said expected concentrating level; and
adjusting said series of geographically located gas concentration data points based on a difference between said expected period of time and said actual period of time for said measured gas concentration to reach said expected concentrating level.

12. The method of determining soil attributes as set forth in claim 8, further comprising the steps of:
repeating said steps of measuring said gas concentration, determining said position, transmitting said position to said controller, and mapping said measured gas concentration with said position to produce a series of geographically located gas concentration data points; and determining a first location at which said air intake is lifted out of the soil and a second location at which it is lowered back into the soil;
determining a first measured gas concentration at said first location and a second measured gas concentration at said second location;
measuring a change between said first measured gas concentration and said second measured gas concentration; and
adjusting said series of geographically located gas concentration data points based on said measured change between said first measured gas concentration and said second measured gas concentration.

13. A method of determining soil attributes, comprising the following steps:
providing a system for determining soil attributes during movement of an associated vehicle, comprising:
an air intake mounted on a soil-working implement of said associated vehicle and in fluid communication with a vacuum pump mounted on said associated vehicle, said air intake and said vacuum pump configured to continuously draw soil gasses from soil through said air intake during movement of said associated vehicle;
at least one gas sensor in fluid communication with said air intake and operable for continuously receiving soil gasses from said air intake and measuring gas concentration levels in said soil gasses received from said air intake during movement of said associated vehicle;
a GPS unit operable to identify a position of said system during movement of said associated vehicle and while said at least one gas sensor receives soil gasses from said air intake and measures gas concentration levels; and
a controller in communication with said at least one gas sensor and said GPS unit and configured to map measurements from said at least one gas sensor relative to a system position as determined by said GPS unit;
continuously drawing soil gasses from soil through said air intake during movement of said associated vehicle;
continuously transmitting said soil gasses to said at least one gas sensor during movement of said associated vehicle;
measuring a gas concentration in said soil gasses with said at least one gas sensor;
transmitting said measured gas concentration to said controller;
determining a position of said air intake with said GPS unit during movement of said air intake with said associated vehicle;
transmitting said position to said controller; and
mapping said measured gas concentration with said position.

14. The method of determining soil attributes as set forth in claim 13, further comprising the step of providing a cleaning/recharging subsystem comprising a source of pressurized air; and a switchable valve in fluid communication with said pressurized air source and with said air intake; said switchable valve operable to selectively fluidly connect said pressurized air source with said air intake.

* * * * *